United States Patent
Niitsu et al.

(10) Patent No.: US 11,123,530 B2
(45) Date of Patent: Sep. 21, 2021

(54) METHOD FOR PRODUCING FINE, HOLLOW PROJECTION TOOL

(71) Applicant: KAO CORPORATION, Tokyo (JP)

(72) Inventors: Takatoshi Niitsu, Utsunomiya (JP); Satoshi Ueno, Utsunomiya (JP)

(73) Assignee: KAO CORPORATION, Tokyo (JP)

(*) Notice: Subject to any disclaimer, the term of this patent is extended or adjusted under 35 U.S.C. 154(b) by 228 days.

(21) Appl. No.: 16/073,174

(22) PCT Filed: Jan. 17, 2017

(86) PCT No.: PCT/JP2017/001428
§ 371 (c)(1),
(2) Date: Jul. 26, 2018

(87) PCT Pub. No.: WO2017/130799
PCT Pub. Date: Aug. 3, 2017

(65) Prior Publication Data
US 2019/0030308 A1    Jan. 31, 2019

(30) Foreign Application Priority Data
Jan. 27, 2016 (JP) .............................. JP2016-013865

(51) Int. Cl.
*A61M 37/00* (2006.01)
*B26F 1/24* (2006.01)
*B81C 1/00* (2006.01)

(52) U.S. Cl.
CPC ........ *A61M 37/0015* (2013.01); *A61M 37/00* (2013.01); *B26F 1/24* (2013.01);
(Continued)

(58) Field of Classification Search
CPC ....... A61M 2037/0053; A61M 37/0015; B26F 1/24
See application file for complete search history.

(56) References Cited

U.S. PATENT DOCUMENTS 5,078,947 A    1/1992    Nishizawa et al.
5,215,088 A    6/1993    Normann et al.
(Continued)

FOREIGN PATENT DOCUMENTS

EP    0 497 620 A2    8/1992
JP    1-110929 A    4/1989
(Continued)

OTHER PUBLICATIONS

Translation of WO-2006025596-A1 (Year: 2006).*
International Search Report (PCT/ISA/210) issued in PCT/JP2017/001428, dated Apr. 11, 2017.

*Primary Examiner* — Marc C Howell
*Assistant Examiner* — John J DeRusso
(74) *Attorney, Agent, or Firm* — Birch, Stewart, Kolasch & Birch, LLP

(57) ABSTRACT

Method for manufacturing fine hollow protruding tool by: bringing a projecting mold part with a heating means into contact from one surface side of a base sheet including a thermoplastic resin, and, while heat-softening the contact section, inserting the projecting mold part into the base sheet, to form a protrusion protruding from the other surface side; and, after a cooling step, withdrawing the projecting mold part from the interior of the protrusion, forming the fine hollow protruding tool. In the protrusion forming step, the protrusion is formed by using a first warp-suppressing means that suppresses warping of the base sheet when the projecting mold part is inserted into the base sheet. In the release step, the fine hollow protruding tool is formed by using a second warp-suppressing means that suppresses warping of the base sheet when the projecting mold part is withdrawn from the interior of the protrusion.

27 Claims, 10 Drawing Sheets

(52) U.S. Cl.
CPC .... *B81C 1/00111* (2013.01); *A61M 2037/003* (2013.01); *A61M 2037/0053* (2013.01); *B81C 2201/034* (2013.01)

(56) References Cited

U.S. PATENT DOCUMENTS

| | | | |
|---|---|---|---|
| 5,383,512 | A | 1/1995 | Jarvis |
| 6,256,533 | B1 | 7/2001 | Yuzhakov et al. |
| 6,931,277 | B1 | 8/2005 | Yuzhakov et al. |
| 2002/0020688 | A1 | 2/2002 | Sherman et al. |
| 2004/0164454 | A1 | 8/2004 | Gartstein et al. |
| 2005/0178760 | A1 | 8/2005 | Chang et al. |
| 2005/0209565 | A1 | 9/2005 | Yuzhakov et al. |
| 2006/0048521 | A1 | 3/2006 | Katayama et al. |
| 2008/0088066 | A1* | 4/2008 | Ferguson .......... A61M 37/0015 264/443 |
| 2009/0234301 | A1* | 9/2009 | Tomono ............ A61M 37/0015 604/272 |
| 2010/0004608 | A1 | 1/2010 | Hamamoto et al. |
| 2011/0162495 | A1* | 7/2011 | Sugiyama ................ B26F 1/14 83/13 |
| 2011/0229688 | A1* | 9/2011 | Cotton .................... B32B 38/04 428/138 |
| 2012/0041337 | A1 | 2/2012 | Ferguson et al. |
| 2017/0239855 | A1 | 8/2017 | Niitsu et al. |

FOREIGN PATENT DOCUMENTS

| | | |
|---|---|---|
| JP | 2570402 B2 | 1/1997 |
| JP | 2002-67163 A | 3/2002 |
| JP | 2003-501162 A | 1/2003 |
| JP | 2003-222422 A | 8/2003 |
| JP | 2006-518675 A | 8/2006 |
| JP | 2010-068840 A | 4/2010 |
| JP | 2013-172833 A | 9/2013 |
| JP | 2017-035432 A | 2/2017 |
| JP | 2017-038903 A | 2/2017 |
| JP | 2017-038904 A | 2/2017 |
| WO | WO 00/74764 A1 | 12/2000 |
| WO | WO-2006025596 A1 * | 3/2006 ........... B29C 51/006 |
| WO | WO 2008/093679 A1 | 8/2008 |

\* cited by examiner (a)

(b)

(a)

(b)

METHOD FOR PRODUCING FINE, HOLLOW PROJECTION TOOL

TECHNICAL FIELD

The present invention relates to a method for manufacturing a fine hollow protruding tool having a hollow interior.

BACKGROUND ART

Delivery of agents with microneedles is receiving attention in recent years, because the same performance as delivering agents with syringes can be achieved without harming the skin and with less pain. Among microneedles, hollow microneedles, in particular, can widen the range of choices of agents to be provided in the hollow portion.

Other than hollow microneedles, there are, in general, self-dissolving-type needles in which the needle itself is made of a dissolvable agent, and coating-type needles in which the needle surface is coated with an agent. In both types, however, the amount of delivery of an agent (the amount of agent held) depends on the shape of the needle. In contrast, hollow-type needles are advantageous in that a large amount of agent can be delivered, irrespective of needle shape.

Such microneedles can be manufactured according to manufacturing methods disclosed in Patent Literature 1 or 2, for example. In the manufacturing method disclosed in Patent Literature 1, a resin body is arranged on an elastic body, and while heating the resin body from the back-surface side of the elastic body, a fine needle is caused to penetrate the resin body to manufacture a fine nozzle. Thus, there is no need to use a mold that includes a fine depression having an inverted shape of the outer shape of the nozzle, and a disposable fine nozzle can be manufactured from a resin.

Patent Literature 2 describes that a hollow microneedle array can be manufactured using a pre-formed mold.

Patent Literature 3 discloses a method for manufacturing microneedles by: arranging a base sheet so as to bridge rod-shaped protrusions; heating the entire base sheet; and causing the sheet to deform into the shape of the rod-shaped protrusions.

CITATION LIST

Patent Literature

Patent Literature 1: JP 2013-172833A
Patent Literature 2: US 2012041337 (A1)
Patent Literature 3: WO 0074764 (A1)

SUMMARY OF INVENTION

The present invention is a method for manufacturing a fine hollow protruding tool having a hollow interior, the method involving: a protrusion forming step of bringing a projecting mold part that includes a heating means into contact from one-surface side of a base sheet including a thermoplastic resin, and, while softening, with heat, a contact section in the base sheet where the projecting mold part contacts the base sheet, inserting the projecting mold part into the base sheet, to form a protrusion that protrudes from another-surface side of the base sheet; a cooling step of cooling the protrusion in a state where the projecting mold part is inserted in an interior of the protrusion; and a release step of withdrawing the projecting mold part from the interior of the protrusion after the cooling step, to form the fine hollow protruding tool. In the protrusion forming step, the protrusion is formed by using a first warp-suppressing means that suppresses warping of the base sheet when the projecting mold part is inserted into the base sheet. In the release step, a second warp-suppressing means that suppresses warping of the base sheet when the projecting mold part is withdrawn from the interior of the protrusion is used.

DESCRIPTION OF EMBODIMENTS

In the fine nozzle manufacturing method described in Patent Literature 1, the entire resin body arranged on the elastic body is heated from the back-surface side of the elastic body by employing, for example, an electrically heated plate; thus, it takes time to heat the entire resin body, making it difficult to improve productivity. Further, because it is necessary to heat the entire resin body arranged on the elastic body, it is difficult to manufacture fine nozzles consecutively.

In the method for manufacturing a fine-through-hole molded product as described in Patent Literature 2, the molds used for molding are expensive, leading to increased costs. Further, there is a low degree of flexibility in microneedle shape and in materials that can be chosen.

In the method described in Patent Literature 3, the entire base sheet is heated; thus, it takes time to heat the entire resin body, making it difficult to improve productivity. Further, at the time of forming the fine needles in an array, it is considered that sections other than where the fine needles are formed are also likely to undergo thermal deformation, making it difficult to control the distance from the bottom of the sheet to the needle's tip end.

The present invention relates to a fine hollow protruding tool manufacturing method capable of overcoming the drawbacks of the aforementioned conventional art.

The invention is described below according to a preferred first embodiment thereof with reference to the drawings.

Figure 1:
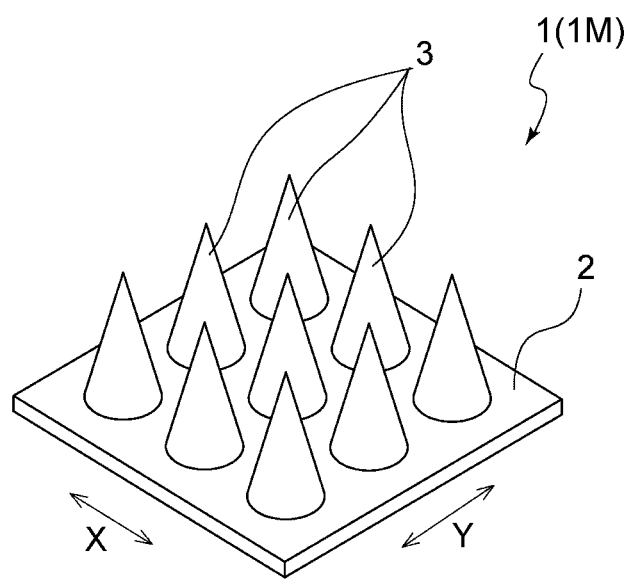
FIG. 1 is a schematic perspective view of an example of a microneedle array manufactured by a method for manufacturing a fine hollow protruding tool of the invention.
Figure 2:
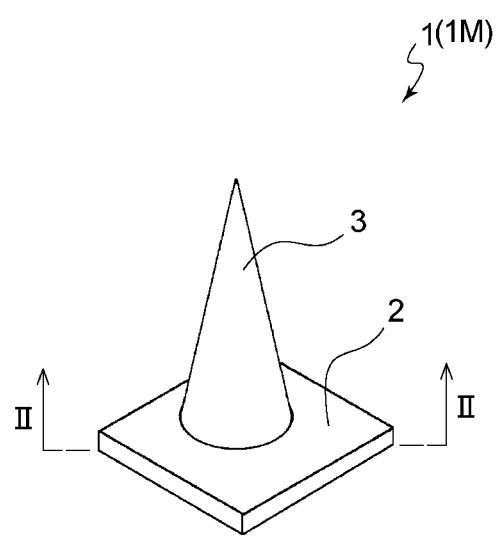
FIG. 2(a) is a perspective view of a single protrusion illustrated in FIG. 1.
FIG. 2(b) is a cross-sectional view taken along line II-II illustrated in FIG. 2(a).
Figure 2:
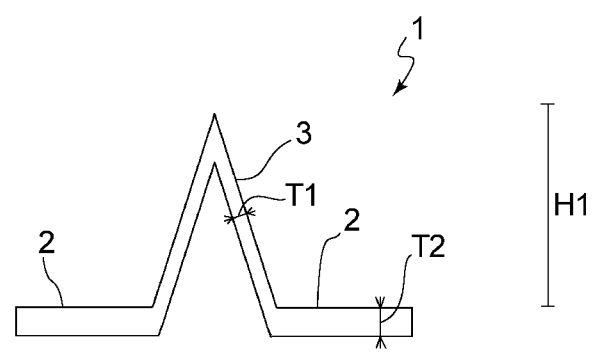

A manufacturing method of the invention is a method for manufacturing a fine hollow protruding tool having a hollow interior. FIG. 1 illustrates a perspective view of a microneedle array 1M as a fine hollow protruding tool 1 of an embodiment manufactured according to a method for manufacturing a fine hollow protruding tool of a first embodiment. The microneedle array 1M of the first embodiment includes: a sheet-like basal portion 2; and a plurality of protrusions 3. The number of protrusions 3, the arrangement of the protrusions 3, and the shape of the protrusion 3 are not particularly limited, but preferably in the microneedle array 1M of the present embodiment, nine circular-conic protrusions 3 are provided in an array (matrix) on the upper surface of the sheet-like basal portion 2. The nine protrusions 3 arranged in an array (matrix) are arranged in three rows along the Y direction, which is the direction in which the later-described base sheet 2A is transported (i.e., the longitudinal direction of the base sheet 2A), and in three columns along the X direction, which is the direction orthogonal to the transporting direction and which is the lateral direction of the base sheet 2A being transported. Note that FIG. 2(a) is a perspective view of the microneedle array 1M, focusing on a single protrusion 3 among the protrusions 3 arranged in an array (matrix) in the microneedle array 1M, and FIG. 2(b) is a cross-sectional view taken along line II-II illustrated in FIG. 2(a). The fine hollow protruding tool 1 illustrated in FIG. 2 includes: a sheet-like basal portion 2; and a single circular-conic protrusion 3 provided so as to stand up on the upper surface of the basal portion 2. As illustrated in FIG. 2, the fine hollow protruding tool 1 is formed so as to have a hollow interior. More specifically, a hollow space is formed so as to extend up to the interior of the protrusion 3, penetrating the basal portion 2. In the fine hollow protruding tool 1, the interior space of the protrusion 3 is formed in a circular-conic shape corresponding to the outer shape of the protrusion 3. It should be noted that, although the protrusion 3 in this fine hollow protruding tool 1 is circular-conic, the protrusion may have a shape other than a circular-conic shape, such as the shape of a truncated circular cone, a circular cylinder, a prism, a pyramid, or a truncated pyramid.

In cases where the fine hollow protruding tool 1 is to be used as a microneedle, in order for the tip end thereof to reach, for example, the stratum corneum, which is the outermost layer, or the dermis, which is a deeper layer, the protrusion height H1 (cf. FIG. 2(b)) of the fine hollow protruding tool 1 is preferably 0.01 mm or greater, more preferably 0.02 mm or greater, and preferably 10 mm or less, more preferably 5 mm or less, and more specifically, preferably from 0.01 to 10 mm, more preferably from 0.02 to 5 mm. The average thickness T1 of the protrusion 3 is preferably 0.005 mm or greater, more preferably 0.01 mm or greater, and preferably 1.0 mm or less, more preferably 0.5 mm or less, and more specifically, preferably from 0.005 to 1.0 mm, more preferably from 0.01 to 0.5 mm. The thickness T2 of the basal portion 2 is preferably 0.01 mm or greater, more preferably 0.02 mm or greater, and preferably 1.0 mm or less, more preferably 0.7 mm or less, and more specifically, preferably from 0.01 to 1.0 mm, more preferably from 0.02 to 0.7 mm.

The tip end size, in diameter, of the protrusion 3 of the fine hollow protruding tool 1 is preferably 0.001 mm or greater, more preferably 0.005 mm or greater, and preferably 0.5 mm or less, more preferably 0.3 mm or less, and more specifically, preferably from 0.001 to 0.5 mm, more preferably from 0.005 to 0.3 mm. The tip end diameter of the protrusion 3 of the fine hollow protruding tool 1 is measured as follows.

{Measurement of Tip End Diameter of Protrusion 3 of Fine Hollow Protruding Tool 1}

Figure 3:
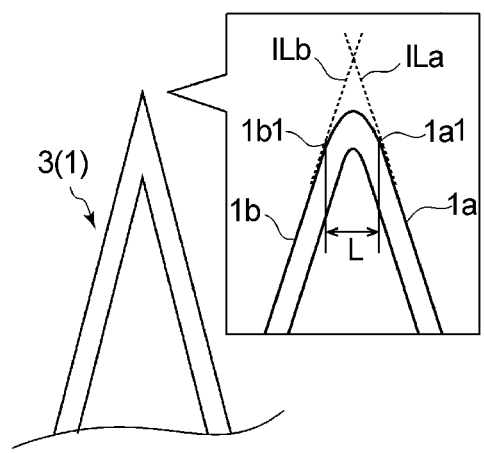
FIG. 3(a) is an explanatory diagram illustrating a method for measuring the tip end diameter of a protrusion of the hollow protruding tool illustrated in FIG. 2(b)
FIG. 3(b) is an explanatory diagram illustrating a method for measuring the tip end diameter of a protrusion in cases where the protrusion has a tip-end opening.
Figure 3:
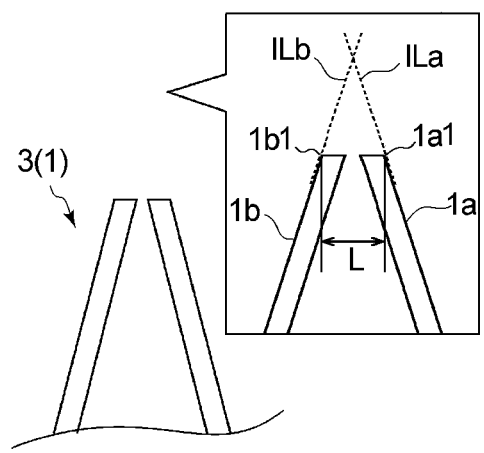

In cases where the tip end of the protrusion 3 is not opened, the tip end portion of the protrusion 3 of the fine hollow protruding tool 1 is observed in an enlarged state under a predetermined magnification using a scanning electron microscope (SEM) or a microscope, as in the SEM image illustrated in FIG. 3(a), for example.

Next, as illustrated in FIG. 3(a), an imaginary straight line ILa is extended along the straight-line portion of one lateral side 1a of the two lateral sides 1a, 1b. Also, an imaginary straight line ILb is extended along the straight-line portion of the other lateral side 1b. The point where the lateral side 1a separates from the imaginary straight line ILa on the tip end side is defined as a first tip end point 1a1, and the point where the other lateral side 1b separates from the imaginary straight line ILb is defined as a second tip end point 1b1. The length L of a straight line that connects the first tip end point 1a1 and the second tip end point 1b1 defined as above is measured using a scanning electron microscope (SEM) or a microscope, and the measured length of the straight line is defined as the tip end diameter of the fine hollow protruding tool 1. In cases where the tip end of the protrusion 3 is opened, as illustrated in FIG. 3(b), imaginary straight lines ILa, ILb are rendered assuming that the protrusion 3 has an opening-side tip end and the intersection point of the imaginary lines is defined as the apex of the protrusion 3, and the aforementioned method illustrated in FIG. 3(a) is employed to measure the tip end diameter.

As illustrated in FIG. 1, the nine protrusions 3 arranged in an array (matrix) on the upper surface of the sheet-like basal portion 2 are preferably arranged such that the center-to-center distance in the longitudinal direction (Y direction) is uniform and the center-to-center distance in the lateral direction (X direction) is uniform, and preferably, the center-to-center distance in the longitudinal direction (Y direction) is the same as the center-to-center distance in the lateral direction (X direction). Preferably, the center-to-center distance in the longitudinal direction (Y direction) between the protrusions 3 is preferably 0.01 mm or greater, more preferably 0.05 mm or greater, and preferably 10 mm or less, more preferably 5 mm or less, and more specifically, preferably from 0.01 to 10 mm, more preferably from 0.05 to 5 mm. The center-to-center distance in the lateral direction (X direction) between the protrusions 3 is preferably 0.01 mm or greater, more preferably 0.05 mm or greater, and preferably 10 mm or less, more preferably 5 mm or less, and more specifically, preferably from 0.01 to 10 mm, more preferably from 0.05 to 5 mm.

Figure 4:
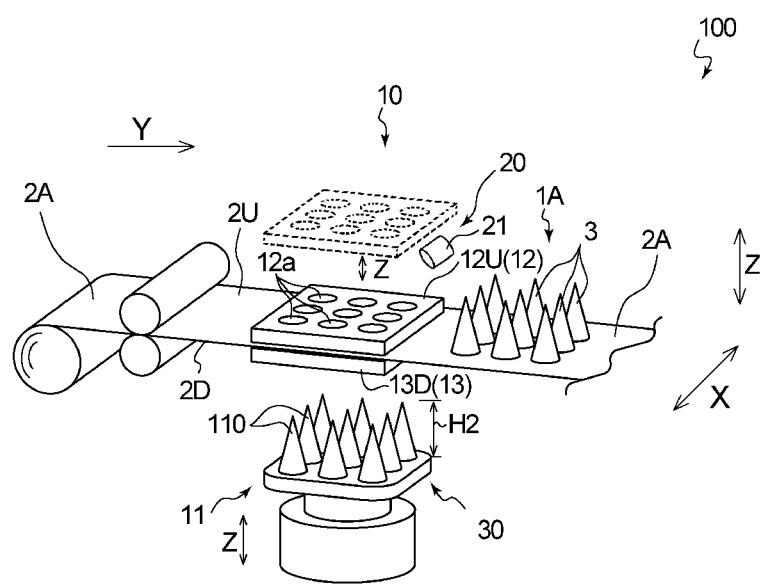
FIG. 4 is a diagram illustrating an overall configuration of a first embodiment of a manufacturing device for manufacturing the fine hollow protruding tool illustrated in FIG. 1.

Next, a method for manufacturing a fine hollow protruding tool of the invention is described with reference to FIGS. 4 to 6, taking a method for manufacturing the aforementioned microneedle array 1M as an example. FIG. 4 illustrates an overall configuration of a manufacturing device 100 according to the first embodiment used for implementing the manufacturing method of the first embodiment. It should be noted that, the protrusions 3 of the microneedle array 1M are actually very small as described above, but for the sake of explanation, the protrusions 3 are illustrated very large in FIG. 4.

The manufacturing device 100 of the first embodiment illustrated in FIG. 4 includes: a protrusion forming section 10 for forming a protrusion 3 in a base sheet 2A; a cooling section 20; and a release section 30 where a projecting mold part 11 is withdrawn. In the following description, the direction in which the base sheet 2A is transported (the longitudinal direction of the base sheet 2A) is referred to as the Y direction, the direction orthogonal to the transporting direction, which is the width direction of the base sheet 2A being transported, is referred to as the X direction, and the thickness direction of the base sheet 2A being transported is referred to as the Z direction. In the present Specification, the projecting mold part 11 is a member including projecting molds 110 which are sections inserted into the base sheet 2A, and in the present embodiment, the projecting mold part 11 is structured so as to be arranged on a disk-shaped foundation. The projecting mold part's structure, however, is not limited thereto, and the projecting mold part may consist only of the projecting mold 110, or the projecting mold part 11 may include a plurality of projecting molds 110 arranged on a platform-like support.

Figure 5:
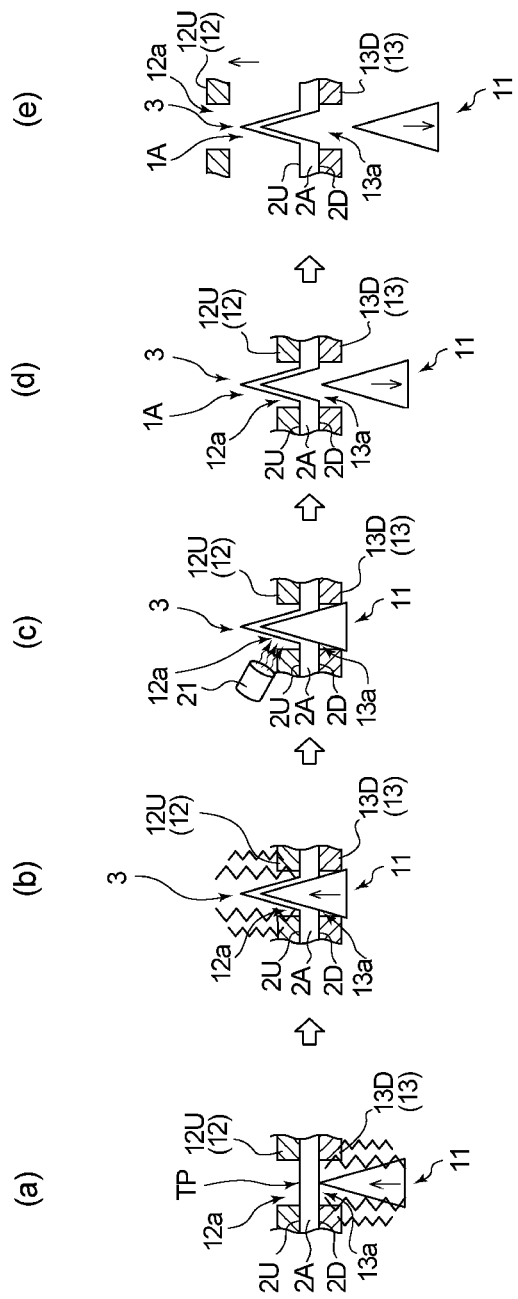
FIGS. 5(a) to 5(e) are diagrams illustrating steps for manufacturing a fine hollow protruding tool by employing the manufacturing device illustrated in FIG. 4.

The protrusion forming section 10 is described using FIGS. 4 and 5. As illustrated in FIG. 4, the protrusion forming section 10 includes a projecting mold part 11 including a heating means (not illustrated). In the manufacturing device 100 of the first embodiment, no other heating means is provided except for the heating means (not illustrated) of the projecting mold part 11. It should be noted that, in this Specification, "no other heating means is provided except for the heating means of the projecting mold part 11" not only refers to cases where other heating means are completely eliminated, but also refers to cases where a means for heating to a temperature below the softening temperature of the base sheet 2A, or to a temperature below the glass transition temperature, is provided. Note, however, that it is preferable to completely eliminate all other heating means. In the manufacturing device 100, the heating means (not illustrated) of the projecting mold part 11 is an ultrasonic vibration device.

In the first embodiment, first, as illustrated in FIG. 4, a continuous base sheet 2A is paid out from an original textile roll of a base sheet 2A formed including a thermoplastic resin, and is transported in the Y direction. Then, when the base sheet 2A has been fed to a predetermined position, the transportation of the base sheet 2A is stopped. In this way, in the first embodiment, the continuous base sheet 2A is transported intermittently.

The base sheet 2A is a sheet that constitutes the basal portion 2 of the fine hollow protruding tool 1 being manufactured, and is formed by including a thermoplastic resin. Examples of the thermoplastic resin include poly-fatty acid esters, polycarbonate, polypropylene, polyethylene, polyester, polyamide, polyamide imide, polyether ether ketone, polyetherimide, polystyrene, polyethylene terephthalates, polyvinyl chloride, nylon resin, acrylic resin, and combinations thereof. From the viewpoint of biodegradability, poly-fatty acid esters are preferably used. Concrete examples of poly-fatty acid esters include polylactic acid, polyglycolic acid, and combinations thereof. Note that the base sheet 2A may be formed of a mixture including, for example, hyaluronic acid, collagen, starch, cellulose, etc., in addition to thermoplastic resin. The thickness of the base sheet 2A is substantially the same as the thickness T2 of the basal portion 2 of the fine hollow protruding tool 1 being manufactured.

Next, in the first embodiment, as illustrated in FIGS. 5(*a*) and 5(*b*), the projecting mold part 11 is brought into contact from the one surface 2D side of the continuous base sheet 2A being transported in the Y direction, and, while softening, with heat, a contact section TP in the base sheet 2A where the projecting mold part contacts the base sheet, the projecting mold part 11 is inserted into the base sheet 2A, to form protrusions 3 that protrude from the other surface 2U side of the base sheet 2A (protrusion forming step). In the protrusion forming step, the protrusions 3 are formed by using a first warp-suppressing means that suppresses warping of the base sheet 2A when the projecting mold part 11 is inserted into the base sheet 2A. In the first embodiment, the first warp-suppressing means used in the protrusion forming step is arranged on the other surface 2U side of the base sheet 2A and is a support 12 that supports the base sheet 2A when the projecting mold part 11 is inserted into the base sheet 2A. The support 12 is arranged at a position corresponding to the predetermined position to which the base sheet 2A is fed.

The projecting mold part 11 is shaped so as to have a circular-conic section with a sharp tip end, to correspond to the outer shape of the circular-conic protrusion 3 of the fine hollow protruding tool 1 being manufactured. More specifically, in the manufacturing device 100 of the first embodiment, as illustrated in FIG. 4, the projecting mold part 11 includes projecting molds 110 corresponding to the number and arrangement of the protrusions 3 on the microneedle array 1M to be manufactured and corresponding substantially to the outer shape of each protrusion 3; and nine circular-conic projecting molds 110 are provided corresponding to the nine circular-conic protrusions 3. In this way, in the protrusion forming step of the first embodiment, by using the projecting mold part 11 having a plurality of (nine) projecting molds 110, a plurality of (nine) protrusions 3 are formed in an array. In the manufacturing device 100 of the first embodiment, the projecting mold part 11 is arranged such that the respective tip ends of the projecting molds 110 face upward, and is movable at least vertically in the thickness direction (Z direction). Preferably, in the manufacturing device 100 of the first embodiment, the projecting mold part 11 can be moved vertically in the thickness direction (Z direction) by an electric actuator (not illustrated). Note that it is preferable that the heating means (not illustrated) of the projecting mold part 11 is operated from immediately before the projecting mold part 11 comes into contact with the base sheet 2A to immediately before the base sheet reaches the next step (cooling step).

The operation of the projecting mold part 11 and heating conditions of the heating means (not illustrated) of the projecting mold part 11, such as the operation etc. of the heating means (not illustrated) of the projecting mold part 11, are controlled by a control means (not illustrated) provided to the manufacturing device 100 of the first embodiment.

As described above, in the manufacturing device 100 of the first embodiment, the heating means (not illustrated) of the projecting mold part 11 is an ultrasonic vibration device.

As regards the ultrasonic vibration of the projecting mold part 11 by the ultrasonic vibration device, from the viewpoint of forming the protrusion 3, the frequency thereof is preferably 10 kHz or greater, more preferably 15 kHz or greater, and preferably 50 kHz or less, more preferably 40 kHz or less, and more specifically, preferably from 10 to 50 kHz, more preferably from 15 to 40 kHz. Further, from the viewpoint of forming the protrusion 3, the amplitude of the ultrasonic vibration of the projecting mold part 11 by the ultrasonic vibration device is preferably 1 μm or greater, more preferably 5 μm or greater, and preferably 60 μm or less, more preferably 50 µm or less, and more specifically, preferably from 1 to 60 µm, more preferably from 5 to 50 µm.

The shape of the projecting mold part 11 on the tip-end side only needs to be shaped so as to correspond to the outer shape of the protrusion 3 of the fine hollow protruding tool 1 being manufactured. The height H2 (cf. FIG. 4) of the projecting mold 110 of the projecting mold part 11 is formed equal to or slightly higher than the height H1 of the fine hollow protruding tool 1 being manufactured, and is preferably 0.01 mm or greater, more preferably 0.02 mm or greater, and preferably 30 mm or less, more preferably 20 mm or less, and more specifically, preferably from 0.01 to 30 mm, more preferably from 0.02 to 20 mm. The tip end diameter D1 (cf. FIG. 6) of the projecting mold 110 of the projecting mold part 11 is preferably 0.001 mm or greater, more preferably 0.005 mm or greater, and preferably 1 mm or less, more preferably 0.5 mm or less, and more specifically, preferably from 0.001 to 1 mm, more preferably from 0.005 to 0.5 mm. The tip end diameter D1 of the projecting mold 110 of the projecting mold part 11 is measured as described below.

The base diameter D2 of the projecting mold 110 of the projecting mold part 11 is preferably 0.1 mm or greater, more preferably 0.2 mm or greater, and preferably 5 mm or less, more preferably 3 mm or less, and more specifically, preferably from 0.1 to 5 mm, more preferably from 0.2 to 3 mm. From the viewpoint of easily achieving sufficient strength, the tip end angle α of the projecting mold 110 of the projecting mold part 11 is preferably 1 degree or greater, more preferably 5 degrees or greater. From the viewpoint of obtaining a protrusion 3 having an appropriate angle, the tip end angle α is preferably 60 degrees or less, more preferably 45 degrees or less, and more specifically, preferably from 1 to 60 degrees, more preferably from 5 to 45 degrees. The tip end angle α of the projecting mold part 11 is measured as follows.

{Measurement of Tip End Diameter of Projecting Mold 110 of Projecting Mold Part 11}

The tip end portion of the projecting mold 110 of the projecting mold part 11 is observed in an enlarged state under a predetermined magnification using a scanning electron microscope (SEM) or a microscope. Next, as illustrated in FIG. 6, an imaginary straight line ILc is extended along the straight-line portion of one lateral side 11a of the two lateral sides 11a, 11b. Also, an imaginary straight line ILd is extended along the straight-line portion of the other lateral side 11b. The point where the lateral side 11a separates from the imaginary straight line ILc on the tip end side is defined as a first tip end point 11a1, and the point where the other lateral side 11b separates from the imaginary straight line ILd is defined as a second tip end point 11b1. The length D1 of a straight line that connects the first tip end point 11a1 and the second tip end point 11b1 defined as above is measured using a scanning electron microscope (SEM) or a microscope, and the measured length of the straight line is defined as the tip end diameter of the projecting mold 110.

{Measurement of Tip End Angle α of Projecting Mold 110 of Projecting Mold Part 11}

Figure 6:
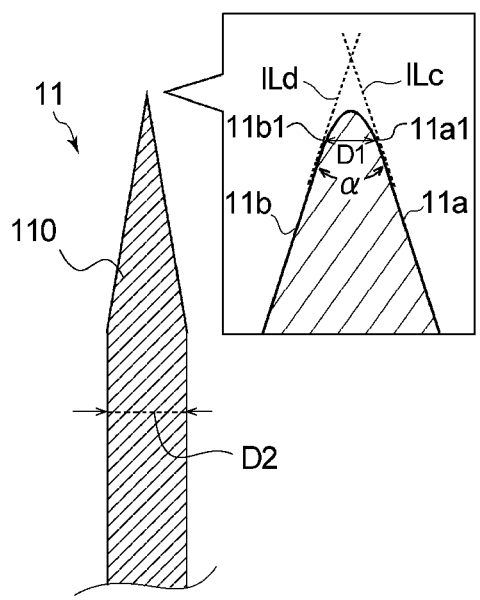
FIG. 6 is an explanatory diagram illustrating a method for measuring the tip end angle of a projecting mold part.

The tip end portion of the projecting mold 110 of the projecting mold part 11 is observed in an enlarged state under a predetermined magnification using a scanning electron microscope (SEM) or a microscope, as in the SEM image illustrated in FIG. 6, for example. Next, as illustrated in FIG. 6, an imaginary straight line ILc is extended along the straight-line portion of one lateral side 11a of the two lateral sides 11a, 11b. Also, an imaginary straight line ILd is extended along the straight-line portion of the other lateral side 11b. The angle formed between the imaginary straight line ILc and the imaginary straight line ILd is measured using a scanning electron microscope (SEM) or a microscope, and the measured angle is defined as the tip end angle α of the projecting mold 110 of the projecting mold part 11.

The projecting mold part 11 is formed of a high-strength material that is hard to bend/break. Examples of materials for the projecting mold part 11 include metals, such as steel, stainless steel, aluminum, aluminum alloy, nickel, nickel alloy, cobalt, cobalt alloy, copper, copper alloy, beryllium copper, and beryllium copper alloy, and ceramics.

As described above, the first warp-suppressing means used in the protrusion forming step is a support 12 that supports the base sheet 2A, as illustrated in FIG. 4. The support 12 is arranged on the other surface 2U side of the base sheet 2A, and serves to make the base sheet 2A less likely to warp/bend when the projecting mold part 11 is inserted from the one surface 2D side. Thus, the support 12 is arranged so as to support a region other than a region, in the base sheet 2A, into which the projecting mold part 11 is inserted—i.e., a region other than a region, in the base sheet 2A, where the protrusions 3 are formed. In the manufacturing device 100 of the first embodiment, an opening plate 12U having a plurality of openings 12a into which the respective projecting molds 110 of the projecting mold part 11 can be inserted is used as the support 12 arranged as above. The opening plate 12U is formed of a plate-like member extending parallel to the transporting direction (Y direction). The opening plate 12U supports the base sheet 2A in regions other than the openings 12a.

The opening plate 12U may be formed such that a single opening 12a has a greater opening area than the cross-sectional area of the projecting mold 110 so that a plurality of projecting molds 110 of the projecting mold part 11 can be passed through a single opening. In the manufacturing device 100 of the first embodiment, however, the opening plate is formed such that one projecting mold 110 is passed through one opening 12a, as illustrated in FIGS. 5(a) and 5(b).

The opening plate 12U is movable in a direction separating from the direction contacting the base sheet 2A. In the manufacturing device 100 of the first embodiment, the opening plate 12U can move vertically in the thickness direction (Z direction) by an electric actuator (not illustrated).

The operation of the opening plate 12U is controlled by a control means (not illustrated) provided to the manufacturing device 100 of the first embodiment.

The material constituting the support 12 may be the same as the material of the projecting mold part 11, and may be formed of a synthetic resin, for example.

The opening diameter of each opening 12a of the opening plate 12U, which is the support 12, is from 0.1 to 20 mm, more preferably from 0.2 to 10 mm.

In the manufacturing device 100 of the first embodiment, an ultrasonic vibration device is used as the heating means (not illustrated) of the projecting mold part 11, and the opening plate 12U is used as the first warp-suppressing means. In the manufacturing device 100 of the first embodiment, the opening plate 12U is arranged on the other surface 2U side (upper surface side) of the base sheet 2A, and a later-described second opening plate 13D, as a second warp-suppressing means, is arranged on the one surface 2D side (lower surface side) of the base sheet 2A. Thus, in the first embodiment, the protrusion forming step is performed in a state where the base sheet 2A is sandwiched between the support 12 and a second support 13. Preferably, in the protrusion forming step of the first embodiment, the projecting molds 110 are passed through the respective openings 13a in the later-described second opening plate 13D from the one surface 2D side (lower surface side) of the base sheet 2A, and made to contact the one surface 2D of the base sheet 2A, as illustrated in FIG. 5(a). Then, at the contact sections TP of the base sheet 2A, the ultrasonic vibration device causes the projecting molds 110 to vibrate ultrasonically, and thereby, the contact sections TP are softened by generating heat at the contact sections TP by friction. Then, as illustrated in FIG. 5(b), while softening the contact sections TP, the projecting mold part 11 is raised from the one surface 2D side (lower surface side) of the base sheet 2A toward the other surface 2U side (upper surface side), and the projecting mold part 11 is inserted into the base sheet 2A, while suppressing warping of the base sheet 2A with the opening plate 12U arranged on the other surface 2U side (upper surface side) of the base sheet 2A, thereby forming protrusions 3 that protrude from the other surface 2U side (upper surface side) of the base sheet 2A by passing through the respective openings 12a of the opening plate 12U.

From the viewpoint of forming the protrusion 3, the heating temperature of the base sheet 2A by heating the projecting mold part 11 is preferably equal to or higher than the glass transition temperature of the base sheet 2A being used to below the melting temperature thereof, and more preferably, equal to or higher than the softening temperature of the base sheet 2A to below the melting temperature thereof. More specifically, the heating temperature is preferably 30° C. or higher, more preferably 40° C. or higher, and preferably 300° C. or lower, more preferably 250° C. or lower, and more specifically, preferably from 30° C. to 300° C., more preferably from 40° C. to 250° C. In cases where the base sheet 2A is heated by using the ultrasonic vibration device as in the first embodiment, the aforementioned heating temperature is employed as the temperature range of a section of the base sheet 2A that comes into contact with the projecting mold 110. On the other hand, in cases where the base sheet 2A is heated by using a heating heater device instead of the ultrasonic vibration device, the heating temperature of the projecting mold part 11 simply needs to be adjusted within the aforementioned range. It should be noted that the glass transition temperature (Tg) is measured according to the following measurement method, and the softening temperature is measured according to JIS K-7196 "Testing method for softening temperature of thermoplastic film and sheeting by thermomechanical analysis".

{Method for Measuring Glass Transition Temperature (Tg)}

The glass transition temperature is determined by measuring the heat quantity by using a DSC measurement device. More specifically, the measurement device used is a differential scanning calorimeter (Diamond DSC) from Perkin Elmer. A 10-mg test piece is sampled from the base sheet. As for the measurement conditions, the temperature is kept constant at 20° C. for 5 minutes, and then the temperature is raised from 20° C. to 320° C. at a rate of 5° C./minute, to obtain a DSC curve wherein the horizontal axis indicates temperature and the vertical axis indicates heat quantity. The glass transition temperature Tg is determined from the DSC curve.

Note that the "glass transition temperature (Tg) of the base sheet" refers to the glass transition temperature (Tg) of the resin constituting the base sheet. In cases where there are a plurality of types of constituent resins and the plurality of glass transition temperatures (Tg) are different from each other, the heating temperature of the base sheet by the heating means is preferably at least equal to or higher than the lowest glass transition temperature (Tg) among the plurality of glass transition temperatures (Tg), and more preferably equal to or higher than the highest glass transition temperature (Tg) among the plurality of glass transition temperatures (Tg).

The same applies to the "softening temperature of the base sheet", as with the glass transition temperature (Tg). In cases where there are a plurality of types of constituent resins in the base sheet and the plurality of softening temperatures are different from each other, the heating temperature of the base sheet by the heating means is preferably at least equal to or higher than the lowest softening temperature among the plurality of softening temperatures, and more preferably equal to or higher than the highest softening temperature among the plurality of softening temperatures.

In cases where the base sheet includes two or more types of resins having different melting points, the heating temperature of the base sheet by the heating means is preferably below the lowest melting point among the plurality of melting points.

If the insertion speed for inserting the projecting mold part 11 into the base sheet 2A is too slow, the resin will get heated and softened excessively, whereas if the insertion speed is too fast, heating and softening will be insufficient. Thus, from the viewpoint of forming the protrusion 3 efficiently, the insertion speed is preferably 0.1 mm/second or greater, more preferably 1 mm/second or greater, and preferably 1000 mm/second or less, more preferably 800 mm/second or less, and more specifically, preferably from 0.1 to 1000 mm/second, more preferably from 1 to 800 mm/second. The softening time is the time from when the elevation of the heated-state projecting mold part 11 is stopped until the next step (cooling step) is performed while keeping the projecting mold part 11 inserted in the interior of the protrusion 3. Although a too-long softening time will result in excessive heating, from the viewpoint of supplementing insufficient heating, the softening time is preferably 0 seconds or longer, more preferably 0.1 seconds or longer, and preferably 10 seconds or less, more preferably 5 seconds or less, and more specifically, preferably from 0 to 10 seconds, more preferably from 0.1 to 5 seconds.

From the viewpoint of forming the protrusion 3 efficiently, the insertion height of the projecting mold part 11 inserted into the base sheet 2A is preferably 0.01 mm or greater, more preferably 0.02 mm or greater, and preferably 10 mm or less, more preferably 5 mm or less, and more specifically, preferably from 0.01 to 10 mm, more preferably from 0.02 to 5 mm. Herein, "insertion height" refers to the distance between the apex of the projecting mold part 11 and the other surface 2U (upper surface) of the base sheet 2A in a state where the projecting mold part 11 is inserted furthest in the base sheet 2A. So, the insertion height in the protrusion forming step refers to the distance measured in the perpendicular direction from the other surface 2U to the apex of the projecting mold part 11 in a state where the projecting mold part 11 has been inserted furthest in the protrusion forming step and the projecting mold part 11 has emerged from the other surface 2U of the base sheet 2A.

Next, in the manufacturing device 100 of the first embodiment, as illustrated in FIG. 5(c), a cooling section 20 is provided subsequent to the protrusion forming section 10. The cooling section 20 includes, for example, a cold air blowing device (not illustrated). In the first embodiment, after the protrusion forming step, the protrusion 3 is cooled by using this cold air blowing device in a state where the projecting mold part 11 is inserted in the interior of the protrusion 3 (cooling step). More specifically, in the manufacturing device 100 of the first embodiment, the opening plate 12U is arranged on the other surface 2U side (upper surface side) of the base sheet 2A and the later-described second opening plate 13D is arranged on the one surface 2D side (lower surface side) of the base sheet 2A. Thus, in the first embodiment, the cooling step is performed in a state where the base sheet 2A is sandwiched between the support 12 and the second support 13. In the cold air blowing device of the manufacturing device 100 of the first embodiment, as illustrated in FIG. 4, an air vent 21 for blowing cold air is provided on the other surface 2U side (upper surface side) of the base sheet 2A, and cooling is performed by blowing cold air from the air vent 21. Note that the cold air blowing device may be configured so as to cover, in a hollow shape, the entirety of the other surface 2U side (upper surface side) and the one surface 2D side (lower surface side) of the continuous base sheet 2A being transported, so that the continuous base sheet 2A is transported along the transporting direction (Y direction) inside the cold air blowing device, and an air vent 21 for blowing cold air may be provided inside the hollow. Note that the cooling temperature of the cold air blowing device and the cooling time are controlled by the control means (not illustrated) provided to the manufacturing device 100 of the first embodiment. The cold air blowing device may cover the base sheet in a tunnel-like shape or a box-like shape.

In the first embodiment, as illustrated in FIG. 5(c), the protrusion 3 is cooled in a state where the projecting mold part 11 still inserted in the interior of the protrusion 3 by blowing cold air from the air vent 21 arranged on the other surface 2U side (upper surface side) of the base sheet 2A, in a state where the projecting mold part 11 is inserted in the interior of the protrusion 3 by maintaining the position of the projecting mold part 11, without raising the projecting mold part 11. Note that, during cooling, heating of the projecting mold part 11 with the heating device may be continued or stopped, but it is preferable that heating is stopped.

From the viewpoint of forming the protrusion 3, the temperature of the cold air to be blown is preferably −50° C. or higher, more preferably −40° C. or higher, and preferably 26° C. or lower, more preferably 10° C. or lower, and more specifically, preferably from −50° C. to 26° C., more preferably from −40° C. to 10° C. From the viewpoint of balancing moldability and processing time, the cooling time for cooling by blowing cold air is preferably 0.01 seconds or longer, more preferably 0.5 seconds or longer, and preferably 60 seconds or less, more preferably 30 seconds or less, and more specifically, preferably from 0.01 to 60 seconds, more preferably from 0.5 to 30 seconds.

In cases where the heating means (not illustrated) of the projecting mold part 11 is ultrasonic vibration as in the first embodiment, the cold air blowing device does not necessarily have to be provided, and cooling can be achieved by simply turning off the vibration of the ultrasonic vibration device. From this viewpoint, using ultrasonic vibration as the heating means is preferable in terms that the device can be simplified and fine hollow protruding tools 1 can be manufactured easily at high speed. Further, heat is less likely to be transmitted to sections of the base sheet 2A that are not in contact with the projecting mold part 11 and cooling is performed efficiently by stopping the application of ultrasonic vibration; this is advantageous in that deformation is less likely to occur in sections other than the section being molded.

Next, in the manufacturing device 100 of the first embodiment, as illustrated in FIGS. 4 and 5(d), a release section 30 is provided subsequent to the cooling section 20. In the first embodiment, the projecting mold part 11 is withdrawn from the interior of the protrusion 3 after the cooling step, to form a fine hollow protruding tool 1 (release step). In the release step, a second warp-suppressing means that suppresses warping of the base sheet 2A is used when the projecting mold part 11 is withdrawn from the interior of the protrusion 3, to thereby form the fine hollow protruding tool 1. In the first embodiment, the second warp-suppressing means used in the release step is arranged on the one surface 2D side of the base sheet 2A, and the second warp-suppressing means is a second support 13 that supports the base sheet 2A when the projecting mold part 11 is withdrawn from the base sheet 2A. Like the support 12, the second support 13 is arranged at a position corresponding to the predetermined position to which the base sheet 2A is fed.

The second warp-suppressing means used in the release step is a second support 13 that supports the base sheet 2A, as illustrated in FIGS. 4 and 5. The second support 13 is arranged on the one surface 2D side of the base sheet 2A, and serves to make the base sheet 2A less likely to warp/bend when the projecting mold part 11 is withdrawn from the one surface 2D side. Thus, the second support 13 is arranged so as to support a region other than a region, in the base sheet 2A, from which the projecting mold part 11 is withdrawn—i.e., a region other than a region, in the base sheet 2A, where the protrusions 3 are formed. In the manufacturing device 100 of the first embodiment, a second opening plate 13D having a plurality of openings 13a into which the respective projecting molds 110 of the projecting mold part 11 can be inserted is used as the second support 13 arranged as above. The second opening plate 13D is formed of a plate-like member extending parallel to the transporting direction (Y direction). The second opening plate 13D supports the base sheet 2A in regions other than the openings 13a.

The second opening plate 13D may be formed such that a single opening 13a has a greater opening area than the cross-sectional area of the projecting mold 110 so that a plurality of projecting molds 110 of the projecting mold part 11 can be passed through a single opening 13a. In the manufacturing device 100 of the first embodiment, however, the second opening plate 13D is formed such that one projecting mold 110 is passed through one opening 13a, as illustrated in FIGS. 5(a) to 5(d). Further, in the manufacturing device 100 of the first embodiment, the openings 13a of the second opening plate 13D are respectively arranged concentrically with the respective openings 12a of the opening plate 12U, which is the first warp-suppressing means. Thus, the openings 12a, 13a of the pair of the opening plate 12U and the second opening plate 13D sandwiching the base sheet 2A have a region overlapping one another in the thickness direction (Z direction).

In the manufacturing device 100 of the first embodiment, the openings 12a of the opening plate 12U and the openings 13a of the second opening plate 13D have the same opening shape. Note that the shape of the openings 12a, 13a as viewed from the upper surface side of the opening plates 12U, 13D is not particularly limited; in the manufacturing device 100 of the first embodiment, the openings are both circular, and the opening diameter of the openings 12a, 13a is the same.

In the manufacturing device 100 of the first embodiment, the shape of the opening plate 12U and the second opening plate 13D is not particularly limited; in the first embodiment, the opening plates are formed in a plate shape. The length, in the Y direction, of each of the plate-like opening plate 12U and second opening plate 13D is substantially the same as the length, in the Y direction, of the projecting mold part 11, and the opening plate's length in the X direction is substantially the same as the length, in the X direction, of the projecting mold part 11.

The second opening plate 13D may be movable in a direction separating from the direction contacting the base sheet 2A, but in the manufacturing device 100 of the first embodiment, the second opening plate is fixed. In cases where the second opening plate 13D is made movable in a direction separating from the base sheet 2A, the second opening plate 13D may be rendered movable vertically in the thickness direction (Z direction) by an electric actuator (not illustrated).

In cases where the second opening plate 13D is made movable in a direction separating from the base sheet 2A, the operation of the second opening plate 13D is to be controlled by a control means (not illustrated) provided to the manufacturing device 100 of the first embodiment.

The material constituting the second support 13 may be the same as the material constituting the support 12 or the material of the projecting mold part 11, and may be formed of a synthetic resin, for example.

The opening diameter of each opening 13a of the second opening plate 13D, which is the second support 13, is the same as the opening diameter of the opening 12a of the opening plate 12U, and more specifically, is preferably from 0.1 to 20 mm, more preferably from 0.2 to 10 mm.

In the manufacturing device 100 of the first embodiment, the opening plate 12U is arranged on the other surface 2U side (upper surface side) of the base sheet 2A, and the second opening plate 13D is arranged on the one surface 2D side (lower surface side) of the base sheet 2A. Thus, in the first embodiment, the release step is performed in a state where the base sheet 2A is sandwiched between the opening plate 12U, which is the support 12 in the protrusion forming step, and the second opening plate 13D, which is the second support 13. Preferably, in the first embodiment, the cooling step is performed in a state where the base sheet 2A is sandwiched between the support 12 and the second support 13 as illustrated in FIG. 5(c), and thereafter, blowing of cold air from the air vent 21 is stopped, and then, as illustrated in FIG. 5(d), the projecting mold part 11 is lowered from the other surface 2U side (upper surface side) of the base sheet 2A toward the one surface 2D side (lower surface side) to withdraw the projecting mold part 11 from the base sheet 2A while suppressing warping of the base sheet 2A with the second opening plate 13D arranged on the one surface 2D side (lower surface side) of the base sheet 2A. In this way, a precursor 1A of a continuous microneedle array—which becomes a microneedle array 1M including hollow-interior protrusions 3—is formed.

The precursor 1A of the microneedle array formed as above is then transported downstream in the transporting direction (Y direction) after raising the opening plate 12U, which is arranged on the other surface 2U side (upper surface side) of the base sheet 2A, to a position higher than the height of the protrusions 3 of the precursor 1A, as illustrated in FIG. 5(e). Thereafter, the precursor is cut within a predetermined range in a cutting step, and in this way, it is possible to manufacture a microneedle array 1M, as a fine hollow protruding tool 1 of the first embodiment including a sheet-like basal portion 2 and a plurality of protrusions 3 as illustrated in FIG. 1. By repeating the aforementioned steps, fine hollow protruding tools 1 can be manufactured continuously and efficiently on the other surface 2U side (upper surface side) of the base sheet 2A.

The microneedle array 1M manufactured as above may be further shaped into a predetermined shape in subsequent steps, or the base sheet 2A may be adjusted in advance into a desired shape before the step of inserting the projecting mold part 11.

As described above, in the manufacturing method of the first embodiment for manufacturing a microneedle array 1M by using the manufacturing device 100, in the protrusion forming step, as illustrated in FIG. 5(b), the protrusions 3 are formed by using a first warp-suppressing means that suppresses warping of the base sheet 2A when the projecting mold part 11 is inserted into the base sheet 2A; and in the release step, as illustrated in FIG. 5(d), a second warp-suppressing means that suppresses warping of the base sheet 2A when the projecting mold part 11 is withdrawn from the interior of the protrusions 3 is used, to thereby form the fine hollow protruding tool 1. Thus, fine hollow protruding tools 1 having a hollow interior can be manufactured with excellent precision.

Further, the first warp-suppressing means used in the protrusion forming step of the first embodiment is a support 12 that supports the base sheet 2A, as illustrated in FIGS. 4 and 5(b). Thus, fine hollow protruding tools 1 can be manufactured through simple steps only, and thus cost increases can be suppressed. Further, the second warp-suppressing means used in the release step of the first embodiment is a second support 13 that supports the base sheet 2A as illustrated in FIGS. 4 and 5(d). Thus, fine hollow protruding tools 1 can be manufactured through simple steps only, and thus cost increases can be suppressed.

Further, in the first embodiment, as illustrated in FIGS. 5(a) and 5(b), the protrusion forming step is performed in a state where the base sheet 2A is sandwiched between the support 12 and the second support 13. Thus, fine hollow protruding tools 1 having a hollow interior can be manufactured with even better precision. In addition to the protrusion forming step, also the cooling step and the release step are performed in a state where the base sheet 2A is sandwiched between the support 12 and the second support 13, as illustrated in FIGS. 5(c) and 5(d). Thus, fine hollow protruding tools 1 having a hollow interior can be manufactured with particularly excellent precision.

Further, in the first embodiment, as illustrated in FIG. 5, the protrusion forming step and the release step are performed in a state where the support 12 and the second support 13 are arranged so as to support a region other than a region, in the base sheet 2A, into which the projecting mold part 11 is inserted—i.e., a region other than a region, in the base sheet 2A, where the protrusions 3 are formed. Thus, fine hollow protruding tools 1 having a hollow interior can be manufactured with even better precision.

Further, in the first embodiment, as illustrated in FIG. 4, the support 12 used in the protrusion forming step is an opening plate 12U, and the second support 13 used in the release step is a second opening plate 13D. Thus, fine hollow protruding tools 1 can be manufactured through simple steps only, and thus cost increases can be suppressed. Further, in the first embodiment, as illustrated in FIG. 5, one projecting mold 110 is passed through one opening 12a of the opening plate 12U used in the protrusion forming step and one opening 13a of the second opening plate 13D used in the release step. Thus, fine hollow protruding tools 1 having a hollow interior can be manufactured with even better precision.

Further, in the first embodiment, as illustrated in FIG. 5(a), the contact section TP of the base sheet 2A in contact with the projecting mold part 11 is softened only at the contact section TP by frictional heat when ultrasonic vibration, which is the heating means (not illustrated) of the projecting mold part 11, is effected. Thus, fine hollow protruding tools 1 can be manufactured continuously and efficiently while saving energy. In contrast, in cases where the entire resin needs to be heated to the same temperature as the projecting mold part, not only is energy efficiency poor, but also various other problems may arise—such as pitch discrepancies between protrusions, distortion of the sheet, and difficulty in continuously transporting the sheet—due to the entire sheet getting soft. The present invention, on the other hand, is advantageous in that heat by heating with the projecting mold part 11 is transmitted efficiently to the contact section TP, and peripheral sections thereof are in an environment where heating can be left only to natural progression; thus, the aforementioned problems are prevented because only the section to be processed (the contact section) is heated.

Further, as described above, in the manufacturing device 100 of the first embodiment, the control means (not illustrated) controls the operations of the projecting mold part 11, the heating condition of the heating means (not illustrated) of the projecting mold part 11, the cooling temperature of the cold air blowing device, and the cooling time. Thus, by controlling, for example, the insertion height of the projecting mold part 11 in the protrusion forming step with the control means (not illustrated), the insertion amount of the projecting mold part 11 into the base sheet 2A can be changed easily, and the protrusion height H1 of the fine hollow protruding tool 1 to be manufactured can be controlled. Further, by controlling at least one of the heating condition of the projecting mold part 11, the softening time of the contact section TP of the base sheet 2A, and the insertion speed of the projecting mold part 11 into the base sheet 2A, the thickness T1, etc., of the protrusion 3 constituting the fine hollow protruding tool 1 can be controlled freely. Stated differently, the shape of the fine hollow protruding tool 1 can be controlled freely by controlling at least one condition selected from a condition of the heating means (not illustrated) of the projecting mold part 11, the insertion height of the projecting mold part 11 into the base sheet 2A in the protrusion forming step, the softening time of the contact section TP of the base sheet 2A, the insertion speed of the projecting mold part 11 into the base sheet 2A, the shape of the projecting mold part 11, and a cooling condition in the cooling step.

Next, the invention will be described according to second to fifth embodiments with reference to the drawings. Note that the description on the second to fifth embodiments mainly focuses on features that are different from those of the foregoing first embodiment, and features that are the same are accompanied by the same reference numbers and explanation thereof is omitted. The explanation given in the first embodiment applies as appropriate to features that are not particularly mentioned below.

Figure 7:
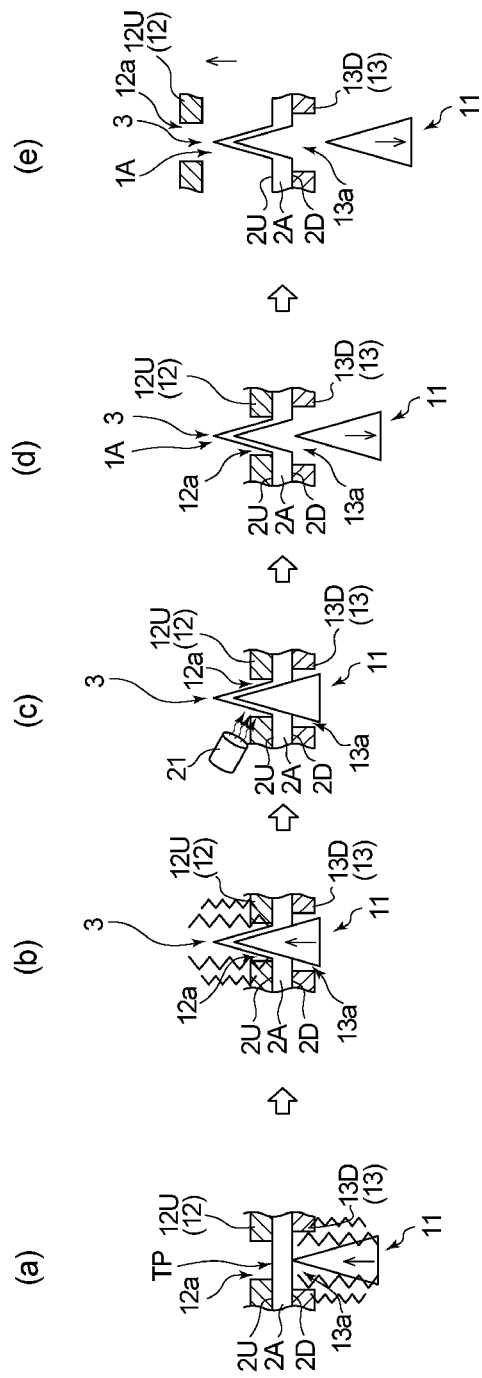
FIGS. 7(a) to 7(e) are diagrams illustrating steps for manufacturing a fine hollow protruding tool by employing a manufacturing device according to a second embodiment.

In the manufacturing device 100 of the first embodiment, the openings 12a of the opening plate 12U and the openings 13a of the second opening plate 13D are formed so as to have the same circular opening shape, as illustrated in FIG. 5. In the manufacturing device 100 according to a second embodiment, however, the opening diameters of the openings 12a, 13a are different, as illustrated in FIG. 7. Preferably, the opening diameter of the opening 13a of the second opening plate 13D arranged on the one surface 2D side (lower surface side) of the base sheet 2A is formed larger than the opening diameter of the opening 12a of the opening plate 12U arranged on the other surface 2U side (upper surface side) of the base sheet 2A. According to the second embodiment using the manufacturing device 100 illustrated in FIG. 7, the openings 12a, 13a are less likely to come into contact when the projecting mold part 11 is inserted into the base sheet 2A in the protrusion forming step, and also, the openings 12a, 13a are less likely to come into contact when the projecting mold part 11 is withdrawn from the base sheet 2A in the release step. Thus, fine hollow protruding tools 1 having a hollow interior can be manufactured with even better precision.

Figure 8:
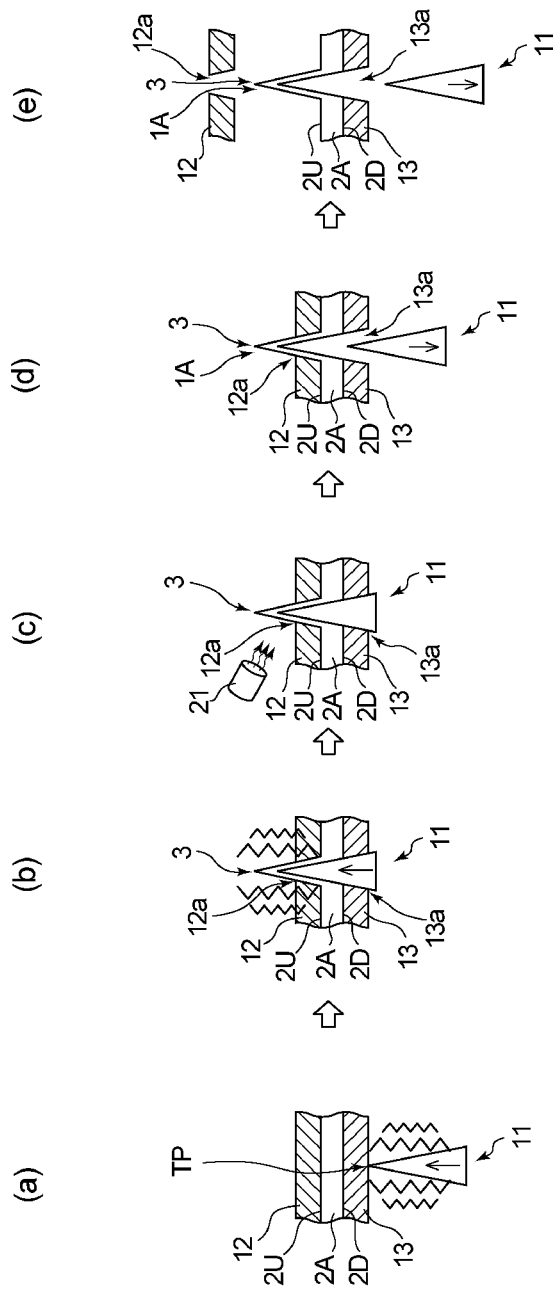
FIGS. 8(a) to 8(e) are diagrams illustrating steps for manufacturing a fine hollow protruding tool by employing a manufacturing device according to a third embodiment.

Next, in the manufacturing device 100 according to a third embodiment, as illustrated in FIG. 8, at least one of the support 12, which is used in the protrusion forming step, and the second support 13, which is used in the release step, initially has no opening 12a, 13a for allowing the projecting mold 110 of the projecting mold part 11 to pass therethrough, and the opening 12a, 13a is formed by being pressed by the projecting mold 110 of the projecting mold part 11 being inserted into the base sheet 2A in the protrusion forming step, as illustrated in FIG. 8(b). Examples of the support 12 and the second support 13 include silicone-made members and elastic members made of rubber, for example.

The support 12 and the second support 13 used in the third embodiment using the manufacturing device 100 illustrated in FIG. 8 are constituted by silicone-made members. Thus, the support 12 and the second support 13 simply need to be arranged so as to support a region including a region, in the base sheet 2A, where the protrusions 3 are to be formed, and thus, fine hollow protruding tools 1 can be manufactured through simple steps only. Note that the support 12 and the second support 13 made of silicone-made members etc. may be removed from the base sheet 2A in/after the release step, but the support(s) may be used as a part of the fine hollow protruding tool 1 being formed.

For example, in an embodiment where the support 12 is not removed from the base sheet 2A in the release step, the thickness of the support 12 may be made thicker, or thinner, than the protrusion height H1 of the protrusion 3. In cases where the thickness of the support 12 is made thicker than the protrusion height H1, the support can function as a protection member for preventing breakage of the protrusions 3 before use. On the other hand, in cases where the thickness of the support 12 is made smaller than the protrusion height H1 of the protrusion 3, the support can serve to control the puncture amount of the protrusion 3 into the skin.

Figure 9:
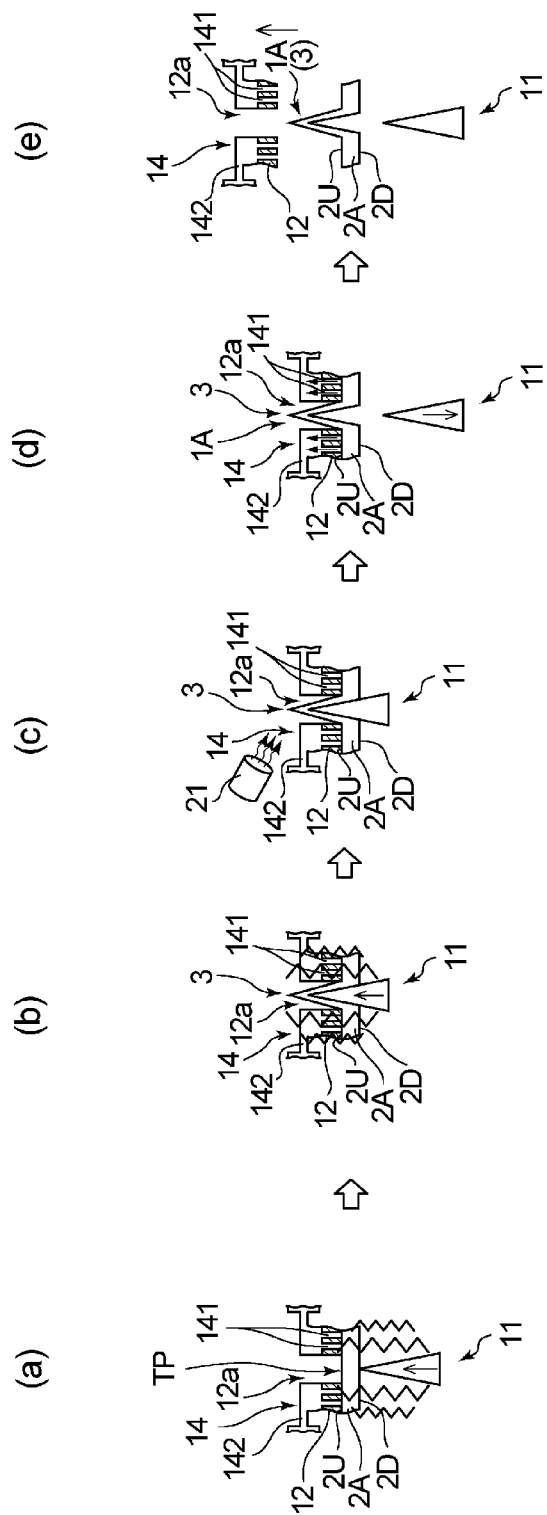
FIGS. 9(a) to 9(e) are diagrams illustrating steps for manufacturing a fine hollow protruding tool by employing a manufacturing device according to a fourth embodiment.

Next, in the manufacturing device 100 according to a fourth embodiment, as illustrated in FIG. 9, the second warp-suppressing means used in the release step is a suction port 14 arranged in the support 12 used in the protrusion forming step. The suction port 14 includes a plurality of suction holes 141 penetrating the support 12, and a suction path 142 connected to the plurality of suction holes 141. The plurality of suction holes 141 are arranged in the peripheral edge section of each opening 12a of the opening plate 12U which is the support 12. The suction path 142 is connected to a suction device (not illustrated) provided outside the manufacturing device 100. By activating the suction device (not illustrated), the other surface 2U side (upper surface side) of the base sheet 2A can be sucked toward the support 12 side via the suction holes 141 connected to the suction path 142. In the manufacturing device 100 of the fourth embodiment, only the support 12 used in the protrusion forming step is the opening plate 12U having a plurality of openings 12a.

In the fourth embodiment using the manufacturing device 100 illustrated in FIG. 9, in the protrusion forming step, in a state where the suction device (not illustrated) is not activated, the protrusions 3 are formed by using the support 12 for suppressing warping of the base sheet 2A when the projecting mold part 11 is inserted into the base sheet 2A, as illustrated in FIGS. 9(a) and 9(b). In the fourth embodiment, in the release step, warping of the base sheet 2A is suppressed by using the suction port 14 to suck the base sheet 2A from the other-surface side (upper surface side) when the projecting mold part 11 is withdrawn from the base sheet 2A, as illustrated in FIG. 9(d). Preferably, in the fourth embodiment, the suction device (not illustrated) is activated after the cooling step, to suck the other surface 2U side (upper surface side) of the base sheet 2A toward the support 12 side via the suction holes 141, and in the release step, a fine hollow protruding tool 1 is formed while suppressing warping of the base sheet 2A when the projecting mold part 11 is withdrawn from the interior of the protrusions 3. As described above, in the release step of the fourth embodiment, warping of the base sheet 2A when withdrawing the projecting mold part 11 is suppressed by suction toward the support 12 side. Thus, a fine hollow protruding tool 1 having a hollow interior can be manufactured with excellent precision. Note that the suction device may be kept in operation during the protrusion forming step.

Figure 10:
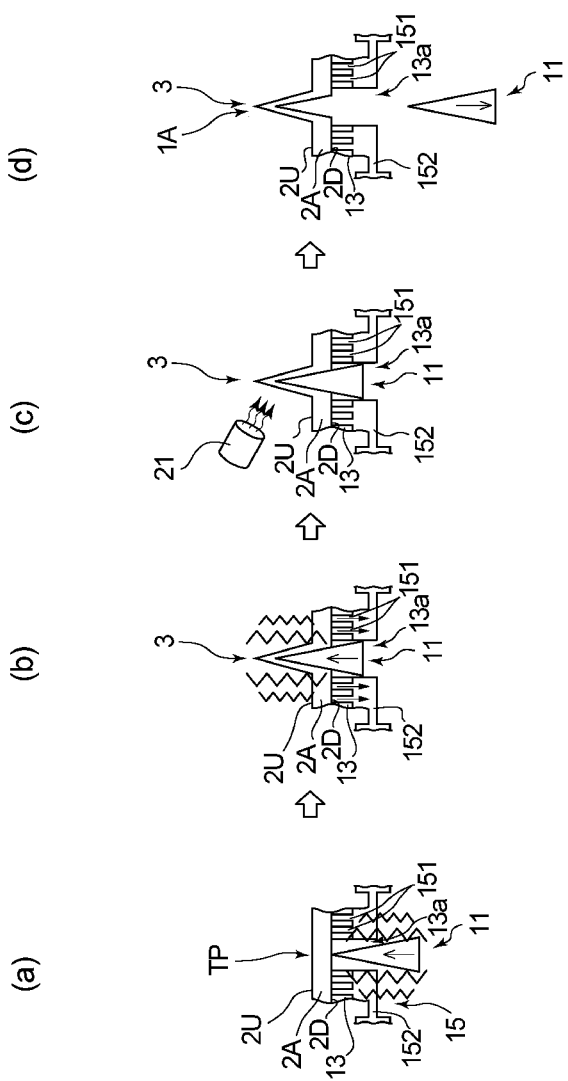
FIGS. 10(a) to 10(d) are diagrams illustrating steps for manufacturing a fine hollow protruding tool by employing a manufacturing device of a fifth embodiment.

Next, in the manufacturing device 100 according to a fifth embodiment, as illustrated in FIG. 10, the first warp-suppressing means used in the protrusion forming step is a second suction port 15 arranged in the second support 13 used in the release step. The second suction port 15 includes a plurality of suction holes 151 penetrating the second support 13, and a suction path 152 connected to the plurality of suction holes 151. The plurality of suction holes 151 are arranged in the peripheral edge section of each opening 13a of the second opening plate 13D which is the second support 13. The suction path 152 is connected to a suction device (not illustrated) provided outside the manufacturing device 100. By activating the suction device (not illustrated), the one surface 2D side (lower surface side) of the base sheet 2A can be sucked toward the second support 13 side via the suction holes 151 connected to the suction path 152. In the manufacturing device 100 of the fifth embodiment, only the second support 13 used in the release step is the second opening plate 13D having a plurality of openings 13a.

In the fifth embodiment using the manufacturing device 100 illustrated in FIG. 10, in the protrusion forming step, the protrusions 3 are formed while suppressing warping of the base sheet 2A when the projecting mold part 11 is inserted into the base sheet 2A by activating the suction device (not illustrated) to suck the one surface 2D side (lower surface side) of the base sheet 2A toward the second support 13 side via the suction holes 151, as illustrated in FIGS. 10(a) and 10(b). In the fifth embodiment, the suction device (not illustrated) is stopped after the cooling step, and in the release step, a fine hollow protruding tool 1 is formed by using the second support 13 that suppresses warping of the base sheet 2A when the projecting mold part 11 is withdrawn from the interior of the protrusions 3, as illustrated in FIG. 10(d). As described above, in the protrusion forming step of the fifth embodiment, warping of the base sheet 2A when inserting the projecting mold part 11 is suppressed by suction toward the second support 13 side. Thus, a fine hollow protruding tool 1 having a hollow interior can be manufactured with excellent precision. Note that the release step may be performed while keeping the suction device in operation after the cooling step.

The present invention has been described above according to preferred first to fifth embodiments thereof, but the invention is not limited to the foregoing embodiments, and can be modified as appropriate.

For example, in the manufacturing devices 100 of the first to fifth embodiments described above, an ultrasonic vibration device is used as the heating means of the projecting mold part 11, but a heater may be used instead.

In the first to fifth embodiments described above, as illustrated in FIG. 4, a continuous base sheet 2A is transported intermittently, and protrusions 3 and fine hollow protruding tools 1 are molded by using a projecting mold part 11 that is movable only vertically in the thickness direction (Z direction). Instead, the continuous base sheet 2A may be transported continuously, and the protrusions 3 and fine hollow protruding tools 1 may be molded by using a projecting mold part 11, a support 12, and a second support 13 of the box-motion type that follow an endless track.

In the first to fifth embodiments, as illustrated in FIG. 4, a projecting mold part 11 that is inserted into the base sheet 2A from below toward above in the thickness direction (Z direction) is used. Instead, the protrusions 3 and fine hollow protruding tools 1 may be molded by using a projecting mold part 11 that is inserted into the base sheet 2A from above toward below in the thickness direction (Z direction).

In the first embodiment, as illustrated in FIG. 4, the opening plate 12U used in the protrusion forming step and the second opening plate 13D used in the release step are arranged so as to sandwich the base sheet 2A, the openings 12a and corresponding openings 13a, respectively in the pair of the opening plate 12U and second opening plate 13D sandwiching the base sheet 2A, overlap one another in the thickness direction (Z direction), and one opening 12a and one opening 13a are arranged at a position corresponding to one projecting mold 110 of the projecting mold part 11. Instead, one opening 12a of the opening plate 12U and one opening 13a of the second opening plate 13D may be arranged at a position corresponding to a plurality of projecting molds 110 of the projecting mold part 11. Alternatively, a plurality of openings 12a of the opening plate 12U may be arranged so as to correspond respectively to the positions corresponding to a plurality of projecting molds 110 of the projecting mold part 11, and one opening 13a of the second opening plate 13D having a larger opening area than the opening 12a may be arranged at the positions of the projecting molds. Alternatively, a plurality of openings 13a of the second opening plate 13D may be arranged so as to correspond respectively to the positions corresponding to a plurality of projecting molds 110 of the projecting mold part 11, and one opening 12a of the opening plate 12U having a larger opening area than the opening 13a may be arranged at the positions of the projecting molds.

With regard to the foregoing embodiments, the present invention further discloses the following method for manufacturing a fine hollow protruding tool.

<1> A method for manufacturing a fine hollow protruding tool having a hollow interior, the method comprising:

a protrusion forming step of bringing a projecting mold part that includes a heating means into contact from one-surface side of a base sheet including a thermoplastic resin, and, while softening, with heat, a contact section in the base sheet where the projecting mold part contacts the base sheet, inserting the projecting mold part into the base sheet, to form a protrusion that protrudes from another-surface side of the base sheet;

a cooling step of cooling the protrusion in a state where the projecting mold part is inserted in an interior of the protrusion; and a release step of withdrawing the projecting mold part from the interior of the protrusion after the cooling step, to form the fine hollow protruding tool, wherein:

in the protrusion forming step, the protrusion is formed by using a first warp-suppressing means that suppresses warping of the base sheet when the projecting mold part is inserted into the base sheet; and in the release step, a second warp-suppressing means that suppresses warping of the base sheet when the projecting mold part is withdrawn from the interior of the protrusion is used.

<2> The method for manufacturing a fine hollow protruding tool as set forth in clause <1>, wherein the first warp-suppressing means is arranged on the other-surface side of the base sheet, and the first warp-suppressing means is a support that supports the base sheet when the projecting mold part is inserted into the base sheet.

<3> The method for manufacturing a fine hollow protruding tool as set forth in clause <2>, wherein:

the second warp-suppressing means is arranged on the one-surface side of the base sheet, and the second warp-suppressing means is a second support that supports the base sheet when the projecting mold part is withdrawn from the base sheet; and the protrusion forming step is performed in a state where the base sheet is sandwiched between the second support and the support of the protrusion forming step.

<4> The method for manufacturing a fine hollow protruding tool as set forth in clause <3>, wherein at least one of the support and the second support supports a region other than a region, in the base sheet, where the protrusion is formed.

<5> The method for manufacturing a fine hollow protruding tool as set forth in clause <3>, wherein at least one of the support and the second support is an opening plate including a plurality of openings into which projecting molds of the projecting mold part can be inserted.

<6> The method for manufacturing a fine hollow protruding tool as set forth in clause <5>, wherein the opening plate is formed such that one of the projecting molds is passed through one of the openings.

<7> The method for manufacturing a fine hollow protruding tool as set forth in clause <3>, wherein at least one of the support and the second support initially has no opening for allowing a projecting mold of the projecting mold part to pass therethrough, and the opening is formed by being pressed by the projecting mold part being inserted into the base sheet in the protrusion forming step.

<8> The method for manufacturing a fine hollow protruding tool as set forth in clause <2>, wherein:

the second warp-suppressing means is a suction port arranged in the support; and in the release step, warping of the base sheet is suppressed by using the suction port to suck the base sheet from the other-surface side when the projecting mold part is withdrawn from the base sheet.

<9> The method for manufacturing a fine hollow protruding tool as set forth in anyone of clauses <1> to <8>, wherein the shape of the fine hollow protruding tool is controlled by controlling at least one condition selected from: a condition of the heating means of the projecting mold part, an insertion height of the projecting mold part into the base sheet, a softening time of the contact section of the base sheet, and an insertion speed of the projecting mold part into the base sheet in the protrusion forming step; the shape of the projecting mold part; and a cooling condition in the cooling step.

<10> The method for manufacturing a fine hollow protruding tool as set forth in anyone of clauses <1> to <9>, wherein:

a continuous base sheet is used as the base sheet; and the fine hollow protruding tools are formed continuously on the other-surface side of the continuous base sheet.

<11> The method for manufacturing a fine hollow protruding tool as set forth in anyone of clauses <1> to <10>, wherein the heating temperature of the base sheet by heating with the projecting mold part is equal to or higher than the glass transition temperature of the base sheet to below the melting temperature thereof.

<12> The method for manufacturing a fine hollow protruding tool as set forth in anyone of clauses <1> to <11>, wherein the heating temperature of the base sheet by heating with the projecting mold part is equal to or higher than the softening temperature of the base sheet to below the melting temperature thereof.

<13> The method for manufacturing a fine hollow protruding tool as set forth in clause <11> or <12>, wherein the heating temperature is from 30° C. to 300° C.

<14> The method for manufacturing a fine hollow protruding tool as set forth in anyone of clauses <1> to <13>, wherein, in the protrusion forming step, no other heating means is provided except for the heating means of the projecting mold part.

<15> The method for manufacturing a fine hollow protruding tool as set forth in anyone of clauses <1> to <14>, wherein the heating means of the projecting mold part is an ultrasonic vibration device; and the contact section is softened by causing ultrasonic vibration of the projecting mold part by the ultrasonic vibration device and generating heat in the contact section by friction.

<16> The method for manufacturing a fine hollow protruding tool as set forth in clause <15>, wherein the frequency of the ultrasonic vibration is from 10 to 50 kHz, more preferably from 15 to 40 kHz.

<17> The method for manufacturing a fine hollow protruding tool as set forth in clause <15> or <16>, wherein the amplitude of the ultrasonic vibration is from 1 to 60 μm, more preferably from 5 to 50 μm.

<18> The method for manufacturing a fine hollow protruding tool as set forth in anyone of clauses <1> to <14>, wherein the heating means of the projecting mold part is a heater device.

<19> The method for manufacturing a fine hollow protruding tool as set forth in anyone of clauses <1> to <18>, wherein a temperature equal to or above the softening temperature of the base sheet is applied only to a section of the base sheet where the projecting mold part is inserted, and a region in the vicinity thereof; and in other regions of the base sheet, temperature rise is left only to natural progression.

<20> The method for manufacturing a fine hollow protruding tool as set forth in anyone of clauses <1> to <19>, wherein the height of the projecting mold part is formed equal to or slightly higher than the height of the fine hollow protruding tool being manufactured.

<21> The method for manufacturing a fine hollow protruding tool as set forth in anyone of clauses <1> to <20>, wherein the height of the projecting mold part is from 0.01 to 30 mm, more preferably from 0.02 to 20 mm.

<22> The method for manufacturing a fine hollow protruding tool as set forth in anyone of clauses <1> to <21>, wherein the tip end diameter of the projecting mold part is from 0.001 to 1 mm, more preferably from 0.005 to 0.5 mm.

<23> The method for manufacturing a fine hollow protruding tool as set forth in anyone of clauses <1> to <22>, wherein the base diameter of the projecting mold part is from 0.1 to 5 mm, more preferably from 0.2 to 3 mm.

<24> The method for manufacturing a fine hollow protruding tool as set forth in anyone of clauses <1> to <23>, wherein the tip end angle of the projecting mold part is from 1 to 60 degrees, more preferably from 5 to 45 degrees.

<25> The method for manufacturing a fine hollow protruding tool as set forth in anyone of clauses <1> to <24>, wherein, in the cooling step, cooling is applied by a cold air blowing device in a state where the projecting mold part is inserted in the interior of the protrusion.

<26> The method for manufacturing a fine hollow protruding tool as set forth in clause <25>, wherein the temperature of the cold air is from −50° C. to 26° C., more preferably from −40° C. to 10° C.

<27> The method for manufacturing a fine hollow protruding tool as set forth in clause <25> or <26>, wherein the cooling time for cooling by blowing the cold air is from 0 to 60 seconds, more preferably from 0.5 to 30 seconds.

<28> The method for manufacturing a fine hollow protruding tool as set forth in anyone of clauses <1> to <24>, wherein, in the cooling step, cooling is performed naturally without cooling with a cold air blowing device.

<29> The method for manufacturing a fine hollow protruding tool as set forth in anyone of clauses <1> to <28>, wherein a plurality of protrusions are formed by inserting the projecting mold part into different positions of the base sheet in the protrusion forming step.

<30> The method for manufacturing a fine hollow protruding tool as set forth in clause <29>, wherein, in the protrusion forming step, a plurality of projecting mold parts arranged in an array are inserted into the base sheet, to form a fine hollow protruding tool including a plurality of protrusions arranged in an array.

<31> The method for manufacturing a fine hollow protruding tool as set forth in anyone of clauses <1> to <30>, wherein the protrusion is a microneedle. <32> The method for manufacturing a fine hollow protruding tool as set forth in clause <31>, wherein the fine hollow protruding tool is a microneedle array in which a plurality of the protrusions are arranged on the base sheet.

EXAMPLES

The invention is described in further detail below according to Examples. The scope of the invention, however, is not limited to the following Examples.

(1) Preparation of Projecting Mold Part 11 of Manufacturing Device:

A projecting mold part made of SUS304, which is a type of stainless steel, was prepared as the projecting mold part 11. The projecting mold part 11 had one circular-conic projecting mold 110. The height H2 (height of the tapered portion) of the projecting mold 110 was 2.5 mm, the tip end diameter D1 was 15 μm, and the base diameter D2 was 0.5 mm.

(2) Preparation of Base Sheet 2A:

A continuous sheet made of polylactic acid (PLA) and having a thickness of 0.3 mm was prepared as the base sheet 2A.

Example 1

A fine hollow protruding tool 1 was manufactured according to the procedure of FIG. 5. The opening plate 12U used in the protrusion forming step and the second opening plate 13D used in the release step were each made of SUS304 and had an opening of 0.5 mm. The opening plate 12U provided with one opening 12a and the second opening plate 13D provided with one opening 13a were used at a position corresponding to the single projecting mold 110 of the projecting mold part 11. The heating means of the projecting mold part 11 was an ultrasonic vibration device. As shown in Table 1, the manufacturing conditions were as follows: frequency of ultrasonic vibration: 20 kHz; amplitude of ultrasonic vibration: 30 μm; insertion height: 0.5 mm; insertion speed: 10 mm/second; softening time: 0.1 seconds; cooling time: 0.5 seconds. Fine hollow protruding tools of Example 1 were manufactured continuously according to the manufacturing conditions described above.

Comparative Example 1

Fine hollow protruding tools according to Comparative Example 1 were manufactured continuously according to the same manufacturing conditions as in Example 1, except that the opening plate 12U used in the protrusion forming step and the second opening plate 13D used in the release step were not arranged.

{Performance Evaluation}

The protrusion height H1 of each fine hollow protruding tool was measured one by one for the manufactured fine hollow protruding tools according to Example 1 and Comparative Example 1 using a microscope. The average value of the results and the difference between the maximum protrusion height and the minimum protrusion height of the measured fine hollow protruding tools are shown in Table 1 below.

TABLE 1

|  | Embodiment | Unit | Example 1 | Comparative Example 1 |
|---|---|---|---|---|
| Manufacturing conditions | Ultrasonic vibration frequency | kHz | 20 | 20 |
|  | Ultrasonic vibration amplitude | μm | 30 | 30 |
|  | Insertion height | mm | 0.5 | 0.5 |
|  | Insertion speed | mm/sec. | 10 | 10 |
|  | Softening time | sec. | 0.1 | 0.1 |
|  | Cooling time | sec. | 0.5 | 0.5 |
| Opening plates | Opening diameter of opening plate | mm | φ0.5 | — |
|  | Opening diameter of second opening plate | mm | φ0.5 | — |

TABLE 1-continued

|  | Embodiment | Unit | Example 1 | Comparative Example 1 |
|---|---|---|---|---|
| Fine hollow protruding tool | Average protrusion height | μm | 496 | 223 |
|  | Maximum protrusion height | μm | 504 | 410 |
|  | Minimum protrusion height | μm | 487 | 111 |
|  | Difference | μm | 17 | 299 |

The results of Table 1 clearly show that the fine hollow protruding tool of Example 1 has better precision in shape than the fine hollow protruding tool of Comparative Example 1. Thus, the method for manufacturing fine hollow protruding tools according to Example 1 can be expected to be able to efficiently and continuously manufacture fine hollow protruding tools having excellent precision in shape.

INDUSTRIAL APPLICABILITY

According to the invention, fine hollow protruding tools having a hollow interior can be manufactured with excellent precision.

The invention claimed is:

1. A method for manufacturing a hollow protruding tool having a hollow interior, the method comprising:
  a protrusion forming step of
    bringing a projecting mold part that includes a heating means into contact from a first surface side of a base sheet including a thermoplastic resin, and,
    while softening, with heat, a contact section in the base sheet where the projecting mold part contacts the base sheet, inserting the projecting mold part into the base sheet, to form a protrusion that protrudes from a second surface side of the base sheet;
  a cooling step of cooling the protrusion in a state where the projecting mold part is inserted in an interior of the protrusion; and
  a release step of withdrawing the projecting mold part from the interior of the protrusion after the cooling step, to form the hollow protruding tool, wherein:
  in the protrusion forming step, the protrusion is formed by using a first warp-suppressing means that suppresses warping of the base sheet when the projecting mold part is inserted into the base sheet;
  in the release step, a second warp-suppressing means that suppresses warping of the base sheet when the projecting mold part is withdrawn from the interior of the protrusion is used; and
  in the protrusion forming step, the contact section of the base sheet is heated to a temperature from equal to or higher than the glass transition temperature of the base sheet to below the melting temperature of the base sheet by heating with the projecting mold part, and other regions of the base sheet are heated to a temperature below the glass transition temperature or are not heated; and
  wherein the heating means of the projecting mold part is an ultrasonic vibration device,
  wherein said protrusion is a microneedle, and
  wherein said hollow protruding tool is a microneedle array in which a plurality of the protrusions are arranged on the base sheet.

2. The method for manufacturing a hollow protruding tool according to claim 1, wherein the first warp-suppressing means is arranged on the second surface side of the base sheet, and the first warp-suppressing means is a support that supports the base sheet when the projecting mold part is inserted into the base sheet.

3. The method for manufacturing a hollow protruding tool according to claim 2, wherein:
  the second warp-suppressing means is arranged on the first surface side of the base sheet, and the second warp-suppressing means is a second support that supports the base sheet when the projecting mold part is withdrawn from the base sheet; and
  the protrusion forming step is performed in a state where the base sheet is sandwiched between the second support and the support of the protrusion forming step.

4. The method for manufacturing a hollow protruding tool according to claim 3, wherein at least one of the support and the second support supports a region other than a region, in the base sheet, where the protrusion is formed.

5. The method for manufacturing a hollow protruding tool according to claim 3, wherein at least one of the support and the second support is an opening plate including a plurality of openings into which projecting molds of the projecting mold part can be inserted.

6. The method for manufacturing a hollow protruding tool according to claim 5, wherein the opening plate is formed such that one of the projecting molds is passed through one of the openings.

7. The method for manufacturing a hollow protruding tool according to claim 3, wherein at least one of the support and the second support initially has no opening for allowing a projecting mold of the projecting mold part to pass therethrough, and an opening is formed by being pressed by the projecting mold part being inserted into the base sheet in the protrusion forming step.

8. The method for manufacturing a hollow protruding tool according to claim 2, wherein:
  the second warp-suppressing means is a suction port arranged in the support; and
  in the release step, warping of the base sheet is suppressed by using the suction port to suck the base sheet from the second surface side when the projecting mold part is withdrawn from the base sheet.

9. The method for manufacturing a hollow protruding tool according to claim 1, wherein the shape of the hollow protruding tool is controlled by controlling at least one condition selected from: a condition of the heating means of the projecting mold part, an insertion height of the projecting mold part into the base sheet, a softening time of the contact section of the base sheet, and an insertion speed of the projecting mold part into the base sheet in the protrusion forming step; the shape of the projecting mold part; and a cooling condition in the cooling step.

10. The method for manufacturing a hollow protruding tool according to claim 1, wherein:
  a continuous base sheet is used as the base sheet; and
  the hollow protruding tool is formed continuously on the second surface side of the continuous base sheet.

11. The method for manufacturing a hollow protruding tool according to claim 1, wherein the heating temperature of the base sheet by heating with the projecting mold part is equal to or higher than the glass transition temperature of the base sheet to below the melting temperature thereof.

12. The method for manufacturing a hollow protruding tool according to claim 1, wherein:
the contact section is softened by causing ultrasonic vibration of the projecting mold part by the ultrasonic vibration device and generating heat in the contact section by friction.

13. The method for manufacturing a hollow protruding tool according to claim 12, wherein the frequency of the ultrasonic vibration is from 10 to 50 kHz.

14. The method for manufacturing a hollow protruding tool according to claim 13, wherein the amplitude of the ultrasonic vibration is from 1 to 60 μm.

15. The method for manufacturing a hollow protruding tool according to claim 1, wherein a temperature equal to or above the softening temperature of the base sheet is applied only to a section of the base sheet where the projecting mold part is inserted, and a region in the vicinity thereof; and in the other regions of the base sheet, temperature rise is left only to natural progression.

16. The method for manufacturing a hollow protruding tool according to claim 1, wherein the height of a projecting mold of the projecting mold part is formed equal to or slightly higher than the height of the hollow protruding tool being manufactured.

17. The method for manufacturing a hollow protruding tool according to claim 1, wherein the height of a projecting mold of the projecting mold part is from 0.01 to 30 mm.

18. The method for manufacturing a hollow protruding tool according to claim 17, wherein a tip end diameter of the projecting mold part is from 0.001 to 1 mm.

19. The method for manufacturing a hollow protruding tool according to claim 18, wherein a base diameter of a projecting mold of the projecting mold part is from 0.1 to 5 mm.

20. The method for manufacturing a hollow protruding tool according to claim 19, wherein a tip end angle of the projecting mold part is from 1 to 60 degrees.

21. The method for manufacturing a hollow protruding tool according to claim 1, wherein, in the cooling step, cooling is applied by blowing cold air in a state where the projecting mold part is inserted in the interior of the protrusion.

22. The method for manufacturing a hollow protruding tool according to claim 21, wherein the temperature of the cold air is from −50° C. to 26° C.

23. The method for manufacturing a hollow protruding tool according to claim 22, wherein the cooling time for cooling by blowing the cold air is from 0.5 to 30 seconds.

24. The method for manufacturing a hollow protruding tool according to claim 1, wherein, in the cooling step, cooling is performed naturally without cooling by blowing cold air.

25. The method for manufacturing a hollow protruding tool according to claim 1, wherein the protrusion step may comprise forming a plurality of protrusions by inserting the projecting mold part into different positions of the base sheet.

26. The method for manufacturing a hollow protruding tool according to claim 1, wherein, in the protrusion forming step, a plurality of projecting molds arranged in an array are inserted into the base sheet, to form an array of protrusions.

27. The method for manufacturing a hollow protruding tool according to claim 5, wherein a plurality of projecting molds of the projecting mold part is passed through a single opening of the opening plate.

* * * * *